United States Patent
Keady et al.

(10) Patent No.: US 9,149,379 B2
(45) Date of Patent: Oct. 6, 2015

(54) DELIVERY DEVICE

(75) Inventors: Fionan Keady, Glenamaddy (IE); Donagh O'Sullivan, Castleroy (IE)

(73) Assignee: Cook Medical Technologies LLC, Bloomington, IN (US)

(*) Notice: Subject to any disclaimer, the term of this patent is extended or adjusted under 35 U.S.C. 154(b) by 630 days.

(21) Appl. No.: 11/879,176

(22) Filed: Jul. 16, 2007

(65) Prior Publication Data

US 2009/0024133 A1   Jan. 22, 2009

(51) Int. Cl.
*A61F 2/06* (2013.01)
*A61F 2/95* (2013.01)
*F16H 19/06* (2006.01)
*F16H 19/04* (2006.01)
*A61F 2/966* (2013.01)

(52) U.S. Cl.
CPC . *A61F 2/95* (2013.01); *A61F 2/966* (2013.01); *A61F 2002/9517* (2013.01); *A61F 2002/9528* (2013.01); *A61F 2002/9534* (2013.01); *A61F 2002/9665* (2013.01); *F16H 19/04* (2013.01); *F16H 19/06* (2013.01); *F16H 2019/0681* (2013.01)

(58) Field of Classification Search
CPC ..................... A61F 2/95–2/97; A61F 2002/9505–2002/9665; F16H 19/02–19/06; F16H 2019/0681–2019/0686
USPC ........................ 623/1.11, 1.12, 1.23; 606/108; 474/148–150; 173/13, 18, 38, 140, 173/151, 215, 216, 170
See application file for complete search history.

(56) References Cited

U.S. PATENT DOCUMENTS

| 1,724,983 A | * | 8/1929 | Weiss .............................. 192/45 |
| 3,132,549 A | * | 5/1964 | Lee .............................. 81/57.29 |
| 3,888,258 A | | 6/1975 | Akiyama |
| 3,897,786 A | | 8/1975 | Garnett et al. |
| 4,559,041 A | | 12/1985 | Razi |
| 4,655,771 A | | 4/1987 | Wallsten |
| 4,921,484 A | | 5/1990 | Hillstead |
| 5,026,377 A | | 6/1991 | Burton et al. |
| 5,275,151 A | | 1/1994 | Shockey et al. |

(Continued)

FOREIGN PATENT DOCUMENTS

| EP | 566 807 A1 | 10/1993 |
| EP | 0 747 021 A2 | 12/1996 |

(Continued)

OTHER PUBLICATIONS

Albee, F. "Bone Surgery with Machine Tools", Scientfiic American, Apr. 1936, pp. 178-181.*

(Continued)

*Primary Examiner* — Darwin Erezo
*Assistant Examiner* — Jonathan Hollm
(74) *Attorney, Agent, or Firm* — Brinks Gilson & Lione

(57) ABSTRACT

A delivery device for deploying an expandable prosthesis and method of use thereof are described. The delivery device comprises an outer catheter that is capable of retracting in a proximal direction and resheathing over the prosthesis in a distal direction. The device comprises a drive pulley that can engage a particular gear set to retract the outer catheter and expose the prosthesis. The drive pulley can also engage another gear set to resheath the outer catheter and recapture the prosthesis between the inner and the outer catheter. A directional switch enables the device to operate between the two modes.

24 Claims, 19 Drawing Sheets

(56) References Cited

U.S. PATENT DOCUMENTS

| | | | |
|---|---|---|---|
| 5,372,600 A | 12/1994 | Beyar et al. | |
| 5,415,664 A | 5/1995 | Pinchuk | |
| 5,433,723 A | 7/1995 | Lindenberg et al. | |
| 5,443,477 A | 8/1995 | Marin et al. | |
| 5,458,615 A | 10/1995 | Klemm et al. | |
| 5,554,894 A | 9/1996 | Sepielli | |
| 5,681,323 A | 10/1997 | Arick | |
| 5,683,451 A | 11/1997 | Lenker et al. | |
| 5,690,644 A | 11/1997 | Yurek et al. | |
| 5,700,269 A | 12/1997 | Pinchuk et al. | |
| 5,702,418 A | 12/1997 | Ravenscroft | |
| 5,707,376 A | 1/1998 | Kavteladze et al. | |
| 5,709,703 A | 1/1998 | Lukic et al. | |
| 5,733,325 A * | 3/1998 | Robinson et al. | 623/1.11 |
| 5,759,186 A | 6/1998 | Bachmann et al. | |
| 5,776,142 A | 7/1998 | Gunderson | |
| 5,833,694 A | 11/1998 | Poncet | |
| 5,906,619 A | 5/1999 | Olson et al. | |
| 5,944,727 A | 8/1999 | Ahari et al. | |
| 5,968,052 A | 10/1999 | Sullivan, III et al. | |
| 5,993,460 A | 11/1999 | Beitelia et al. | |
| 6,093,194 A | 7/2000 | Mikus et al. | |
| 6,146,415 A | 11/2000 | Fitz | |
| 6,162,231 A | 12/2000 | Mikus et al. | |
| 6,168,610 B1 | 1/2001 | Marin et al. | |
| 6,238,402 B1 | 5/2001 | Sullivan, III et al. | 606/108 |
| 6,254,628 B1 | 7/2001 | Wallace et al. | |
| 6,346,118 B1 * | 2/2002 | Baker et al. | 623/1.12 |
| 6,375,676 B1 | 4/2002 | Cox | |
| 6,383,211 B1 | 5/2002 | Stachle | |
| 6,391,050 B1 | 5/2002 | Broome | |
| 6,391,051 B2 | 5/2002 | Sullivan, III et al. | |
| 6,402,760 B1 * | 6/2002 | Fedida | 606/108 |
| 6,413,269 B1 | 7/2002 | Bui et al. | |
| 6,428,566 B1 | 8/2002 | Holt | |
| 6,514,261 B1 | 2/2003 | Randall et al. | |
| 6,520,983 B1 | 2/2003 | Colgan et al. | |
| 6,530,949 B2 | 3/2003 | Konya et al. | |
| 6,592,549 B2 | 7/2003 | Gerdts et al. | |
| 6,599,296 B1 | 7/2003 | Gillick et al. | |
| 6,629,981 B2 | 10/2003 | Bui et al. | |
| 6,669,719 B2 | 12/2003 | Wallace et al. | |
| 6,673,101 B1 | 1/2004 | Fitzgerald et al. | |
| 6,695,862 B2 | 2/2004 | Cox et al. | |
| 6,695,875 B2 | 2/2004 | Stelter et al. | |
| 6,749,627 B2 | 6/2004 | Thompson et al. | |
| 6,755,854 B2 | 6/2004 | Gillick et al. | |
| 6,755,855 B2 | 6/2004 | Yurek et al. | |
| 6,786,918 B1 | 9/2004 | Krivoruchko et al. | |
| 6,808,529 B2 | 10/2004 | Fulkerson | |
| 6,821,291 B2 | 11/2004 | Bolea et al. | |
| 6,860,898 B2 | 3/2005 | Stack et al. | |
| 6,866,669 B2 | 3/2005 | Buzzard et al. | |
| 6,890,317 B2 | 5/2005 | Gerdts et al. | |
| 6,893,458 B2 | 5/2005 | Cox et al. | |
| 6,911,039 B2 | 6/2005 | Shiu et al. | |
| 6,926,732 B2 | 8/2005 | Derus et al. | |
| 6,939,352 B2 | 9/2005 | Buzzard et al. | |
| 6,942,688 B2 | 9/2005 | Bartholf et al. | |
| 6,991,646 B2 | 1/2006 | Clerc et al. | |
| 7,052,511 B2 | 5/2006 | Weldon et al. | |
| 7,122,058 B2 | 10/2006 | Levine et al. | |
| 7,335,224 B2 | 2/2008 | Ohlenschlaeger | |
| 2002/0007206 A1 | 1/2002 | Bui et al. | |
| 2002/0095203 A1 | 7/2002 | Thompson et al. | |
| 2002/0111666 A1 | 8/2002 | Hart et al. | |
| 2002/0183827 A1 | 12/2002 | Derus et al. | |
| 2003/0093084 A1 | 5/2003 | Nissan et al. | |
| 2003/0144671 A1 | 7/2003 | Brooks et al. | |
| 2003/0191516 A1 | 10/2003 | Weldon et al. | |
| 2003/0225445 A1 | 12/2003 | Derus et al. | |
| 2004/0006380 A1 | 1/2004 | Buck et al. | |
| 2004/0010265 A1 | 1/2004 | Karpiel | |
| 2004/0093057 A1 | 5/2004 | Bolduc et al. | |
| 2004/0181239 A1 | 9/2004 | Dorn et al. | |
| 2004/0186547 A1 | 9/2004 | Dorn et al. | |
| 2004/0193180 A1 | 9/2004 | Buzzard et al. | |
| 2004/0215229 A1 | 10/2004 | Coyle | |
| 2004/0220653 A1 | 11/2004 | Borg et al. | |
| 2004/0267282 A1 | 12/2004 | Shkarubo et al. | |
| 2005/0021123 A1 | 1/2005 | Dorn et al. | |
| 2005/0033402 A1 | 2/2005 | Cully et al. | |
| 2005/0033403 A1 | 2/2005 | Ward et al. | |
| 2005/0060016 A1 | 3/2005 | Wu et al. | |
| 2005/0060018 A1 | 3/2005 | Dittman | |
| 2005/0080476 A1 | 4/2005 | Gunderson et al. | |
| 2005/0085890 A1 | 4/2005 | Rasmussen et al. | |
| 2005/0090834 A1 | 4/2005 | Chiang et al. | |
| 2005/0090890 A1 | 4/2005 | Wu et al. | |
| 2005/0113902 A1 | 5/2005 | Geiser et al. | |
| 2005/0131514 A1 * | 6/2005 | Hijlkema et al. | 623/1.12 |
| 2005/0149159 A1 | 7/2005 | Andreas et al. | |
| 2005/0177246 A1 | 8/2005 | Datta et al. | |
| 2005/0182475 A1 | 8/2005 | Jen et al. | |
| 2005/0209670 A1 | 9/2005 | George et al. | |
| 2005/0209685 A1 | 9/2005 | Shifrin et al. | |
| 2005/0240254 A1 | 10/2005 | Austin | |
| 2005/0256562 A1 | 11/2005 | Clerc et al. | |
| 2005/0273151 A1 | 12/2005 | Fulkerson et al. | |
| 2005/0288763 A1 | 12/2005 | Andreas et al. | |
| 2005/0288764 A1 | 12/2005 | Snow et al. | |
| 2005/0288766 A1 | 12/2005 | Plain et al. | |
| 2006/0004433 A1 | 1/2006 | Greenberg et al. | |
| 2006/0009858 A1 | 1/2006 | Levine et al. | |
| 2006/0184224 A1 | 8/2006 | Angel | |
| 2006/0184226 A1 | 8/2006 | Austin | |
| 2009/0030497 A1 | 1/2009 | Metcalf et al. | |
| 2009/0099640 A1 | 4/2009 | Weng | |
| 2010/0168834 A1 | 7/2010 | Ryan et al. | |
| 2010/0262157 A1 | 10/2010 | Silver et al. | |
| 2012/0172963 A1 | 7/2012 | Ryan et al. | |
| 2012/0185031 A1 | 7/2012 | Ryan et al. | |
| 2012/0221093 A1 | 8/2012 | McHugo | |

FOREIGN PATENT DOCUMENTS

| | | |
|---|---|---|
| EP | 1 525 859 A2 | 4/2005 |
| WO | WO 98/53761 A1 | 3/1998 |
| WO | WO 02/05885 A2 | 1/2002 |
| WO | WO 2005/107644 A1 | 11/2005 |
| WO | WO 2007/005799 A1 | 1/2007 |
| WO | WO 2007/022395 A1 | 2/2007 |
| WO | WO 2008/042266 A2 | 4/2008 |
| WO | WO 2009/012061 A1 | 1/2009 |
| WO | WO 2010/040009 A1 | 4/2010 |
| WO | WO 2010/078352 A1 | 7/2010 |
| WO | WO 2011/094527 A1 | 8/2011 |
| WO | WO 2012/099731 A1 | 7/2012 |
| WO | WO 2012/099732 A1 | 7/2012 |
| WO | WO 2012/118638 A1 | 9/2012 |

OTHER PUBLICATIONS

International Search Report and Written Opinion of the International Searching Authority for International Application No. PCT/US2008/069019, dated Oct. 17, 2008, 9 pages.

International Search Report and Written Opinion of the International Searching Authority for International Application No. PCT/US2009/069721, dated Feb. 19, 2010, 9 pages.

International Search Report and Written Opinion of the International Searching Authority for International Application No. PCT/US2011/022903, dated Mar. 24, 2011, 9 pages.

International Search Report and Written Opinion of the International Searching Authority for International Application No. PCT/US2012/020597, dated May 21, 2012, 11 pages.

International Search Report for International Application No. PCT/US2012/020598, dated May 10, 2012, 4 pages.

International Search Report and Written Opinion of the International Searching Authority for International Application No. PCT/US2012/025895, dated Jun. 6, 2012, 12 pages.

* cited by examiner

DELIVERY DEVICE

TECHNICAL FIELD

This invention relates to a medical device and, in particular to a delivery device for a self-expanding prosthesis and a method of delivering and deploying the prosthesis into a body lumen.

BACKGROUND

A self-expanding prosthesis is typically introduced into the body using a delivery device that comprises a push-pull mechanism. The delivery device comprises an outer catheter coaxially disposed and slidable over an inner catheter. The prosthesis is disposed at the distal end of the device in between the inner catheter and the outer catheter. The inner and the outer catheter move coaxially with respect to each other. The prosthesis may be deployed by proximally pulling back the outer catheter relative to the inner catheter until the prosthesis is exposed.

There are numerous drawbacks to the above push-pull delivery device. For example, utilizing a conventional push-pull delivery device may cause the physician to inadvertently use excessive force and pull back the outer catheter too far, thereby prematurely deploying the prosthesis in an incorrect position within a body lumen. At this step in the procedure, repositioning of the prosthesis becomes difficult, if not impossible, because the prosthesis has already radially self-expanded into the body lumen. Additionally, retraction of the outer sheath is not achieved with controlled movement because the physician is manually retracting the outer catheter. Manual retraction of the outer catheter may lead to inadvertent jerking back of the outer catheter. Furthermore, two hands are typically needed to deploy the prosthesis with a push-pull mechanism. One hand may be required to hold the inner catheter while the other hand pulls the outer catheter and slides it back over the inner catheter. The use of two hands prevents the physician from performing another task during the procedure.

Accordingly, in view of the drawbacks of current technology, there is a desire for a delivery system that can increase the control, accuracy and ease of placement during deployment of a prosthesis. Although the inventions described below may be useful for increasing the control, accuracy and ease of placement during deployment of the prosthesis, the claimed inventions may also solve other problems.

SUMMARY

Accordingly, a delivery device is provided comprising an outer catheter that is capable of retracting in a proximal direction and resheathing over the prosthesis in a distal direction.

The invention may include any of the following aspects in various combinations and may also include any other aspect described below in the written description or in the attached drawings.

In a first aspect, an apparatus for delivering an intraluminal device is provided. The apparatus comprises a gear and pulley mechanism comprising a first gear set and a second gear set, a drive pulley adapted to be mechanically coupled to one of the first gear set and the second gear set, and a sheath disposed over an inner elongate sheath, the sheath being in mechanical communication with the drive pulley and adapted to retract in a proximal direction and resheath in a distal direction.

In a second aspect, an apparatus for delivering an intraluminal device is provided. The apparatus comprises a gear and pulley mechanism comprising a first gear set and a second gear set. The apparatus further comprises an inner elongate sheath, the inner elongate sheath being fixed at a proximal end of a handle assembly. The apparatus further comprises an outer elongate sheath disposed over the inner elongate sheath, the outer elongate sheath being coupled to a belt wound around a center drive pulley, the outer elongate sheath adapted to be actuated by the first gear set to be movable in a distal direction relative to the inner elongate sheath, the outer elongate sheath being adapted to be actuated by the second gear set to be movable in a proximal direction relative to the inner elongate sheath; and a stabilizing element extending along a longitudinal axis of the inner and the outer elongate sheaths for fixating the position of the intraluminal device during movement of the outer elongate sheath relative to the inner elongate sheath.

In a third aspect, a method for resheathing an intraluminal device is provided. The method comprises the step of providing a delivery apparatus comprising a gear and pulley mechanism comprising a first gear set and a second gear set, a center drive pulley adapted to be mechanically coupled to one of the first gear set and the second gear set, and a retractable sheath disposed over an inner elongate sheath, the retractable sheath mechanically coupled to the drive pulley by a belt. The method further comprises the step of engaging the center drive pulley with the first gear set and activating a trigger to cause the drive pulley to rotate the belt with the sheath thereon in a distal direction relative to the inner elongate sheath.

BRIEF DESCRIPTION OF THE DRAWINGS

Embodiments will now be described by way of example with reference to the accompanying drawings, in which.

DETAILED DESCRIPTION OF THE PREFERRED EMBODIMENTS

Figure 1:
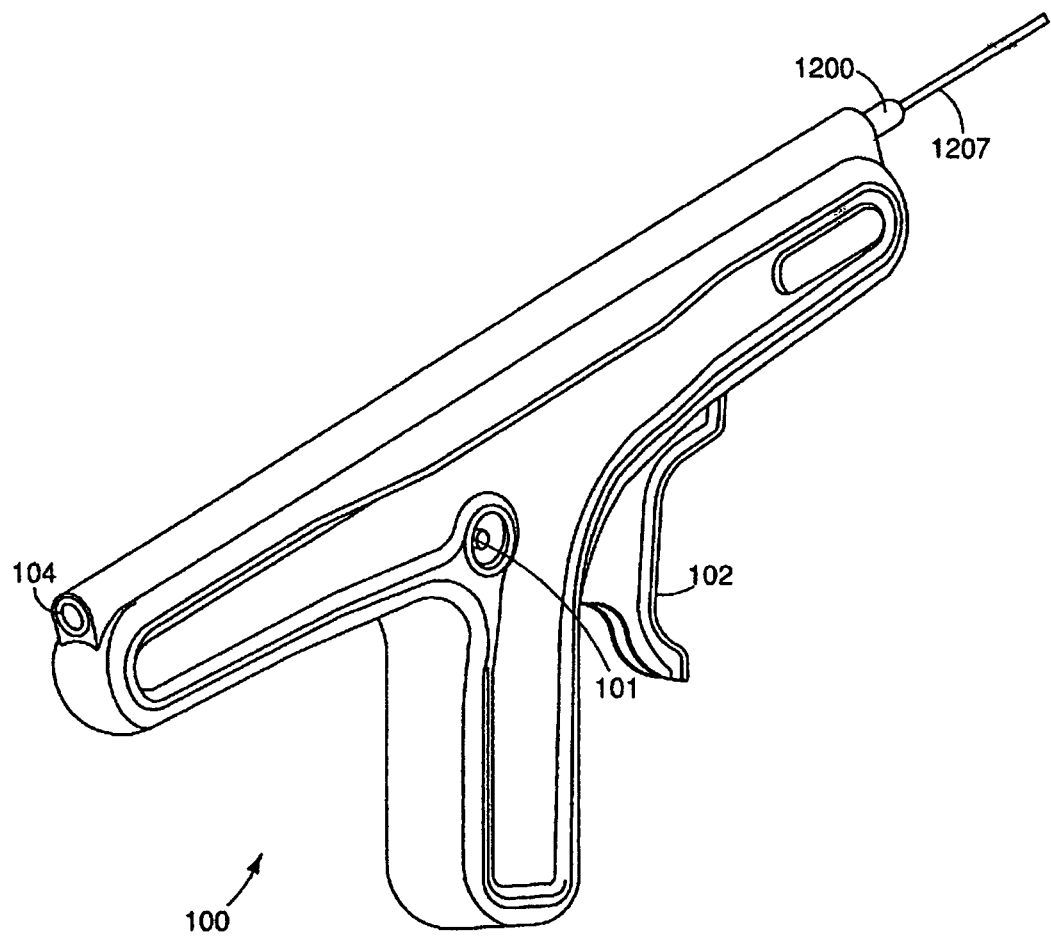
FIG. 1 is a perspective view of a delivery device.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Throughout the specification, the terms "distal" and "distally" shall denote a position, direction, or orientation that is generally away from the physician. Accordingly, the terms "proximal" and "proximally" shall denote a position, direction, or orientation that is generally towards the physician.

Referring now to the drawings in FIGS. 1-26, a delivery device for deploying a self-expanding prosthesis is shown. As will be discussed, the delivery device has the ability to resheath and reposition the prosthesis, thereby substantially increasing the control and accuracy of the deployment process as compared with conventional delivery devices.

Figure 4:
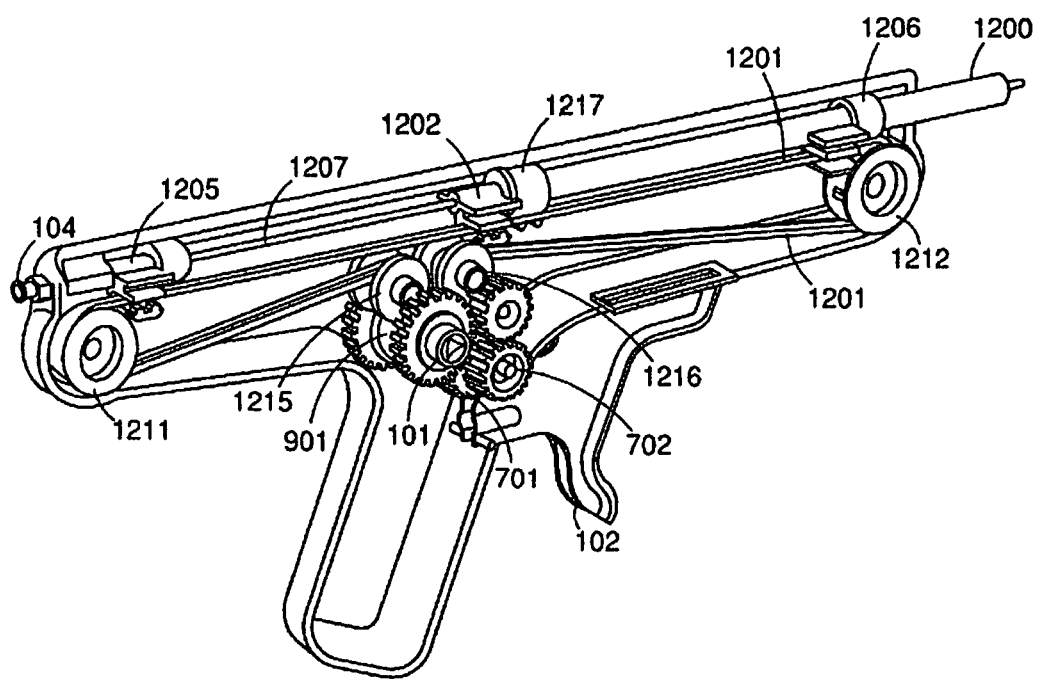
FIG. 4 is a perspective view of the delivery device showing the outer catheter connected to a belt.

FIG. 1 shows an exemplary delivery device 100. The inner catheter 1207 and outer catheter 1200 are shown exiting the distal end of the device 100. The inner catheter 1207 remains fixated to the delivery device 100 at the rear hub 104. The outer catheter 1207 may be affixed to a movable belt 1201 (FIG. 4). Actuation of a spring-loaded trigger 102 pulls the outer catheter 1200 in the proximal direction relative to the inner catheter 1207 to expose the self-expanding prosthesis. A directional switch 101 may be engaged to reverse the direction of the outer catheter 1200 prior to actuating the trigger 102. An internal gear-pulley mechanism enables the bidirectional movement of the outer catheter 1200.

Figure 2:
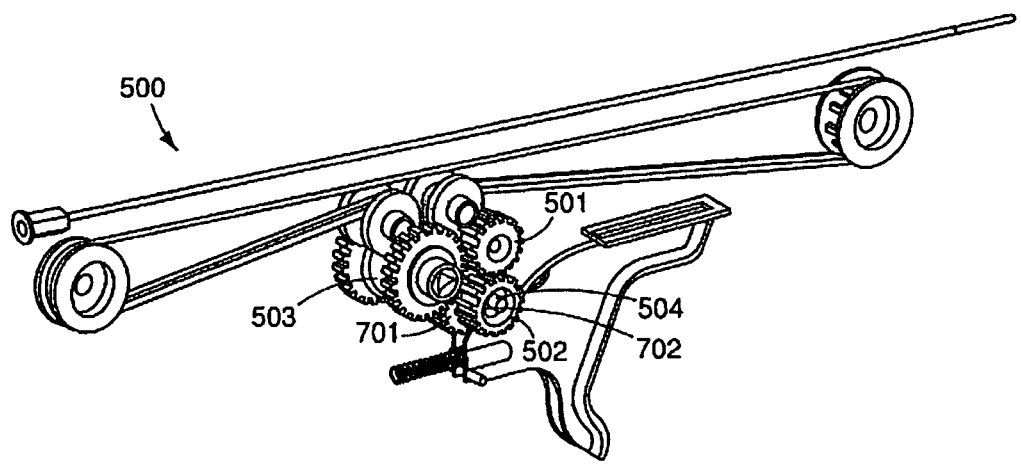
FIG. 2 is a perspective view of a first gear set of the delivery device.

A first gear set resheaths the outer catheter 1200 (i.e, moves the outer catheter 1200 in a distal direction relative to the inner catheter 1207) and a second gear set retracts the outer catheter 1200 (i.e., moves the outer catheter 1200 in a proximal direction relative to the inner catheter 1207). FIG. 2 shows the first gear set 500. The first gear set 500 comprises a first drive gear 502, a first idle gear 501, and a first pulley gear 503. The first drive gear 502 is mechanically engaged with the first idle gear 501. The first idle gear 501 is mechanically engaged with the first pulley gear 503. The first drive gear 502 has a one-directional roller clutch bearing 504. Specifically, the roller clutch bearing 504 is press fit within the inner surface of the first drive gear 502 and allows for rotation of the first drive gear 502 in only one direction, which will be explained in greater detail below.

Figure 3:
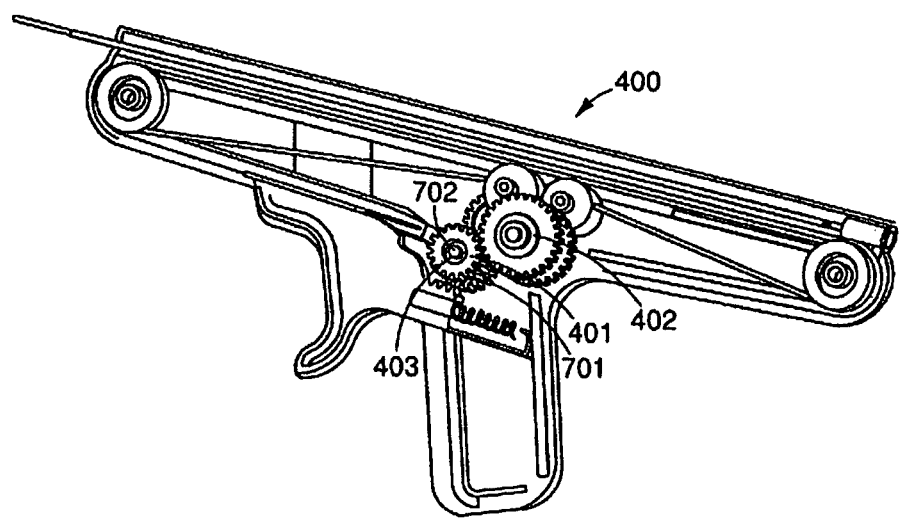
FIG. 3 is a perspective view of a second gear set of the delivery device.

FIG. 3 shows the second gear set 400. The second gear set 400 comprises a second drive gear 401 and a second pulley gear 402. The second drive gear 401 is mechanically coupled to the second pulley gear 402. Similar to the first drive gear 502, the second drive gear 401 also comprises a roller clutch bearing 403 that allows for rotation of the gear 401 in only one direction, which will be explained in greater detail below.

Figure 12:
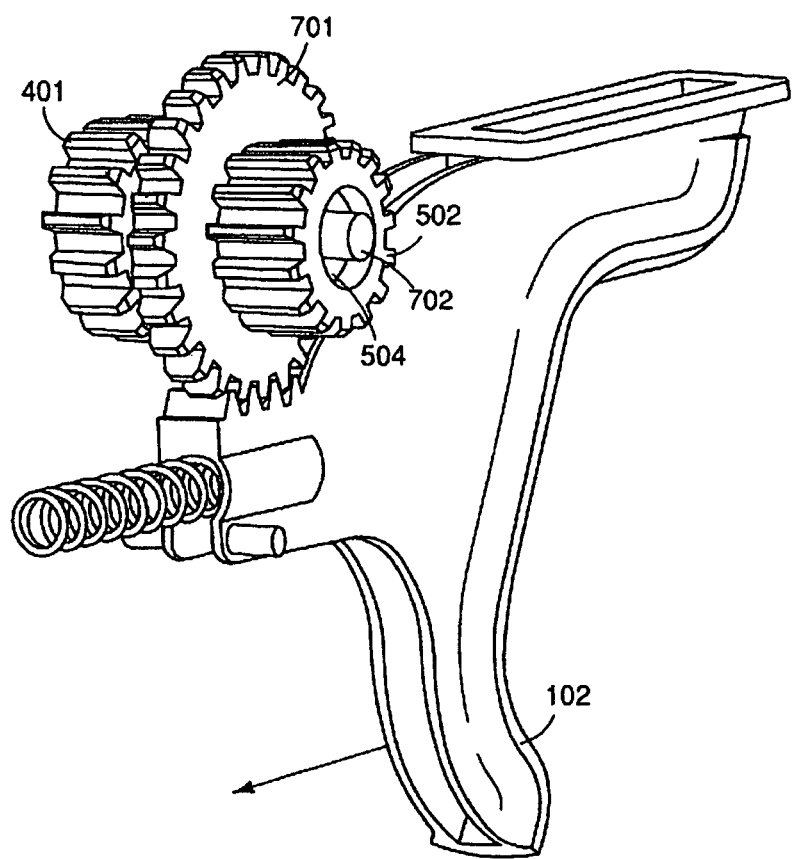
FIG. 12 shows the trigger and the drive gears.
Figure 27:
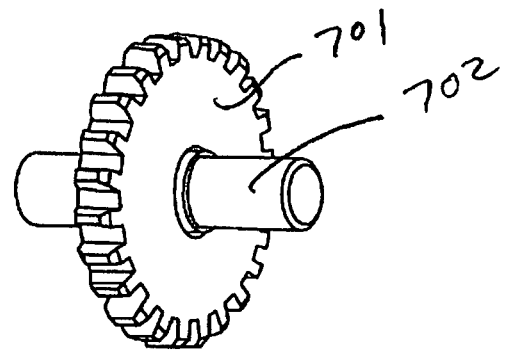
FIG. 27 shows a main drive gear rotationally fixed to the drive shaft.

A drive shaft 702 extends through the clutch bearing 403 of the second drive gear 401 (FIG. 3) and through the clutch bearing 504 of the first drive gear 502 (FIG. 2). A main drive gear 701 is rotationally fixed to the drive shaft 702, as clearly seen in FIG. 27. The main drive gear 701 is also engaged with a trigger 102 (FIG. 12). The trigger 102 includes a rack 709 having complimentary teeth 704 (FIG. 11) that engage with the main drive gear 701.

Figure 5:
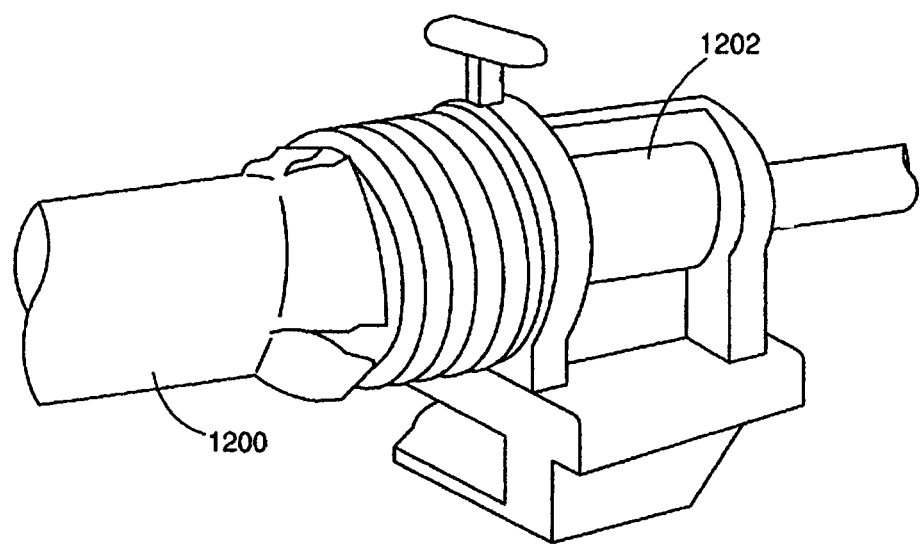
FIG. 5 shows the end of the outer catheter flared and pushed up against a shuttle.
Figure 6:
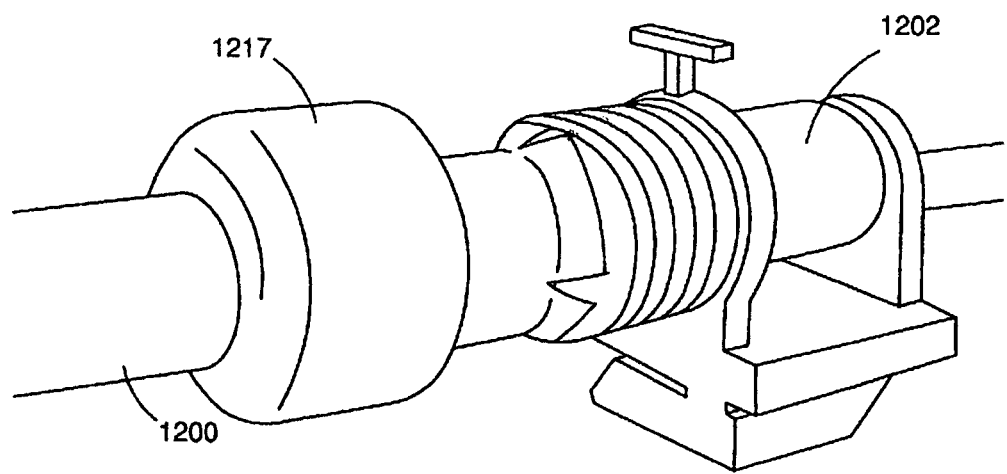
FIG. 6 shows a shuttle cap being screwed to the shuttle to secure the outer catheter to the shuttle.

Proximal and distal movement of the outer catheter 1200 may be allowed by the outer catheter 1200 being connected to a belt 1201, as shown in FIG. 4. The outer catheter 1200 is affixed to a shuttle 1202 and the shuttle 1202 is connected to a belt 1201. FIGS. 5 and 6 show how the outer catheter 1200 is affixed to the shuttle 1202. FIG. 5 shows that the end of the outer catheter 1200 may be flared and pushed up against the shuttle 1202. After abutting the flared end of the outer catheter 1200 against the shuttle 1202, FIG. 6 shows that a shuttle cap 1217 may be coupled to the shuttle 1202. Specifically, the cap 1217 may be screwed onto the threads of the shuttle 1202 to secure the outer catheter 1200 to the shuttle 1202. The inner catheter 1207 may be secured to the rear hub 104 in a similar manner. Other types of attachments of the outer catheter 1200 to the belt 1201 are contemplated.

Figure 7:
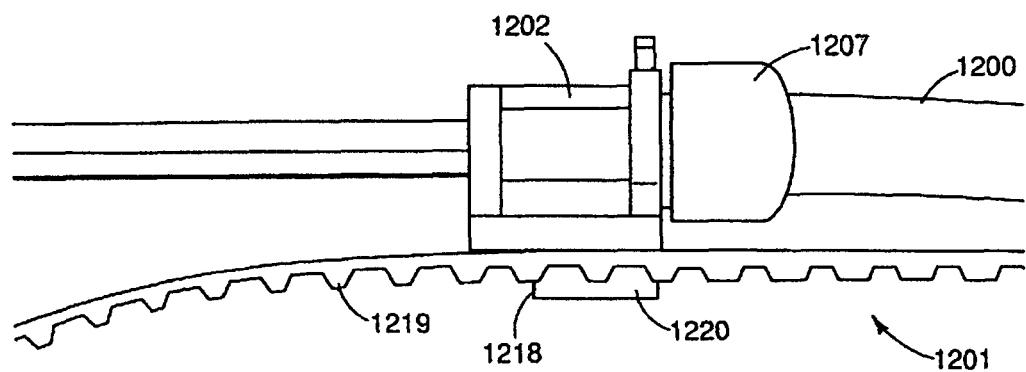
FIG. 7 shows the attachment of the belt to the shuttle and outer catheter.

The attachment of the belt 1201 to the shuttle 1202 and outer catheter 1200 may be seen in FIG. 7. FIG. 7 shows that the shuttle 1202 contains an opening 1218 through which belt 1201 may extend. The shuttle 1202 contains corresponding grooves 1220 that engage with protrusions 1219 of the belt 1201 to establish a secure belt-shuttle connection. Movement of the belt 1201 causes the shuttle 1202 and outer catheter 1200 attached thereto to laterally move along the belt 1201 in the proximal direction or distal direction.

Referring to FIG. 4, activation of the first gear set 500 or the second gear set 400 rotates a center drive pulley 901 and the belt 1201 to cause the shuttle 1202 with the outer catheter 1200 attached thereto to move with the belt 1201. FIG. 4 illustrates possible positions that the outer catheter 1200 may have. The most reverse position of the shuttle 1202 and belt 1201 is indicated at position 1205. The most forward position of the shuttle 1202 and belt 1201 is indicated at position 1206. For purposes of clarity, the shuttle cap 1217 is not shown at positions 1205 and 1206. As the outer catheter 1200 moves along the belt 1201, the inner catheter 1207 remains stationary because the inner catheter 1207 is fixated at the proximal end of the device 100 at the rear hub 104.

Figure 8:
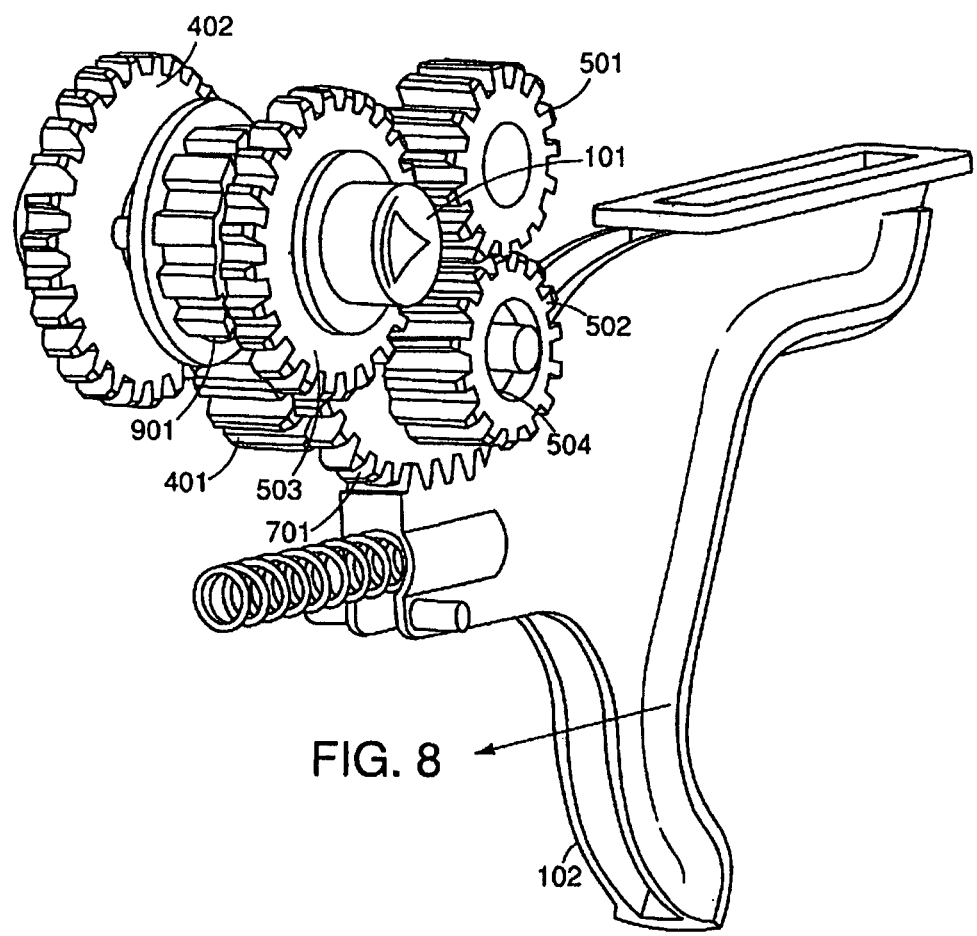
FIG. 8 shows the trigger, drive gears and pulley gears.

Referring to FIG. 8, desired belt 1201 movement is achieved by engaging a center drive pulley 901 with the first pulley gear 503 or the second pulley gear 402. The first pulley gear 503 and the second pulley gear 402 are slidable along a shaft to engage and disengage with the drive pulley 901. The engagement and disengagement may occur by the ribs or protrusions 1000 of the pulley gears 503, 402 slidably engaging with the ribbed slots 902 of the center drive pulley 901. Directional switch 101 allows the first pulley gear 503 or the second pulley gear 402 to engage with the center drive pulley 901. Referring to FIG. 8, the first pulley gear 503, second pulley gear 402, and directional switch 101 extend along a shaft (not shown). Pushing the directional switch 101 against the first pulley gear 503 causes the first pulley gear 503 to engage with the center drive pulley 901 and the second pulley gear 402 to disengage with the center drive pulley 901 along the shaft. At any given time, the center drive pulley 901 may be engaged to either the first pulley gear 503 or the second pulley gear 402.

Figure 9:
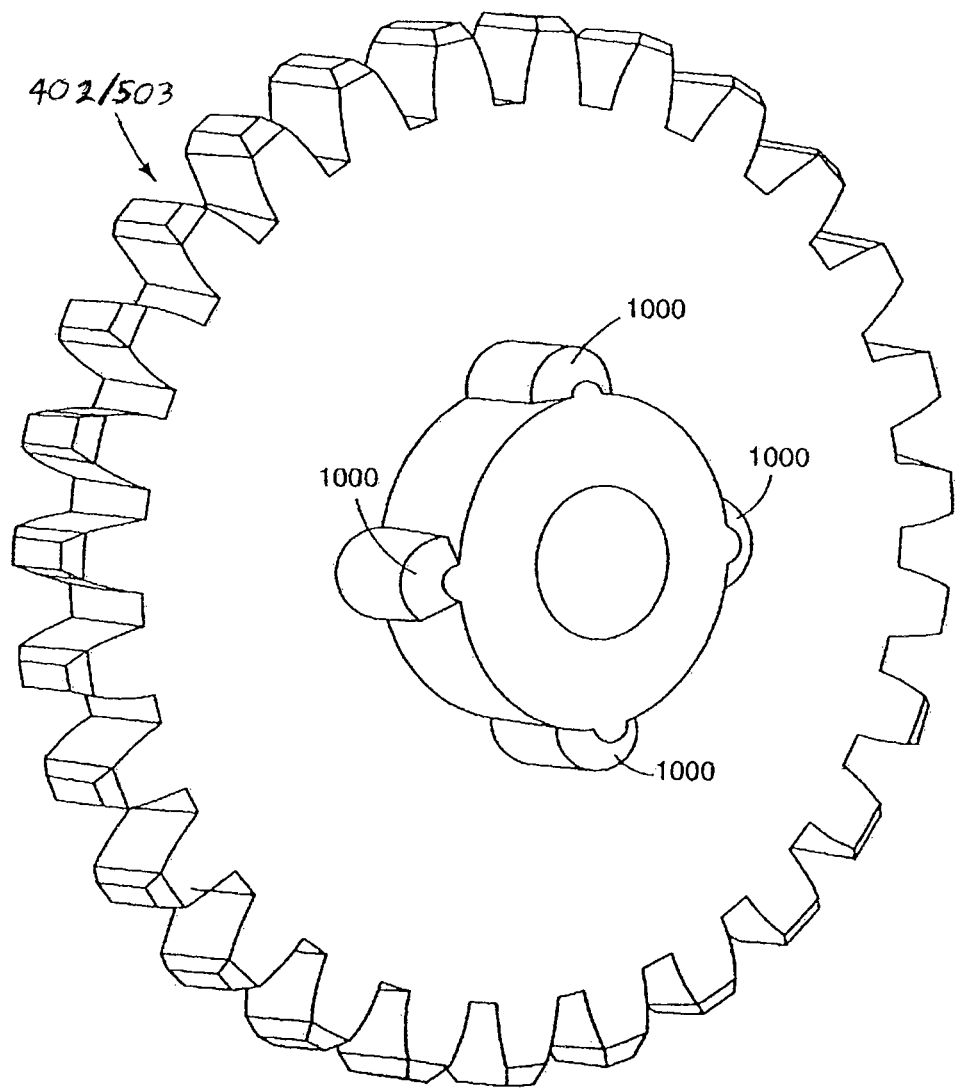
FIG. 9 shows protrusions on one of the faces of the pulley gear that is configured to slot into corresponding slotted ribs located on the center drive pulley.
Figure 10:
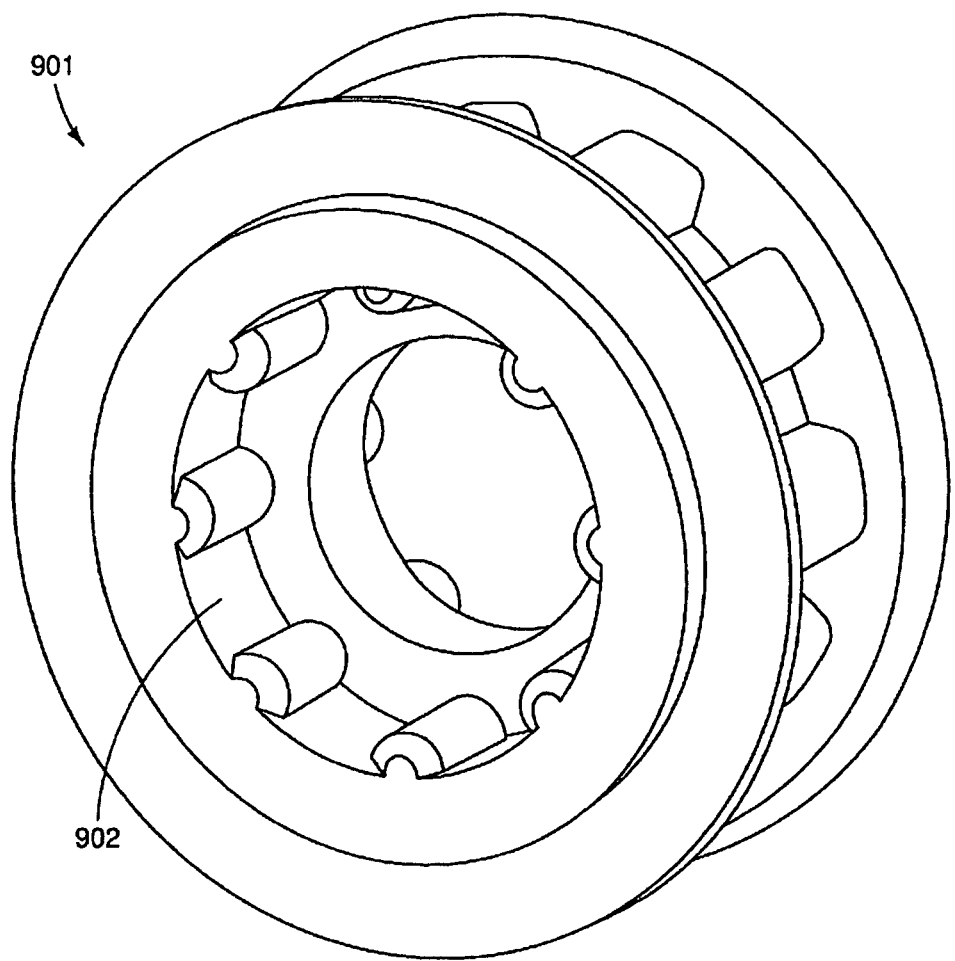
FIG. 10 shows ribbed slots on the center drive pulley that are configured to receive the pulley gears.
Figure 11:
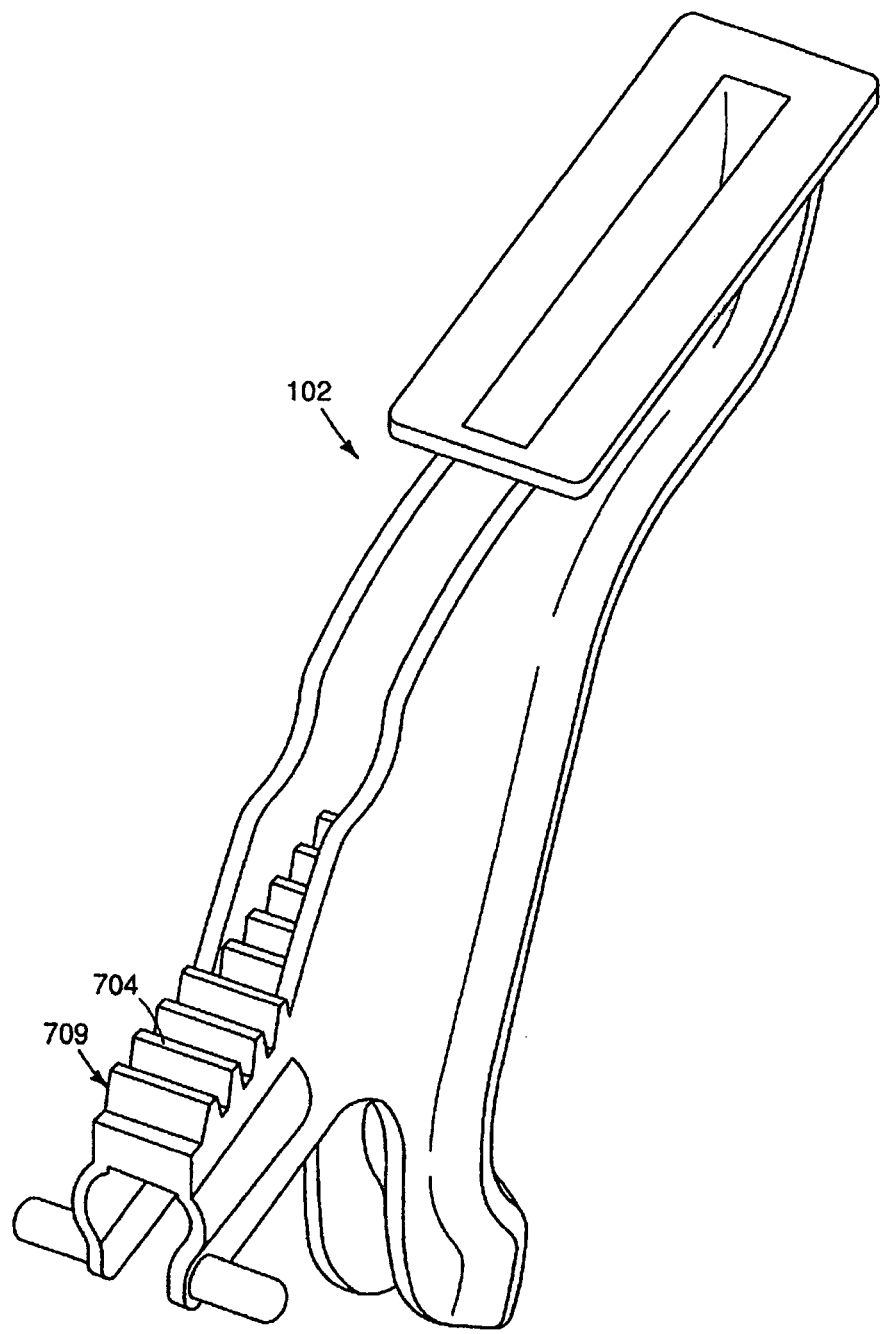
FIG. 11 shows the rack of the trigger of the delivery device.

The engagement of the first or second pulley gears 503, 402 with the center drive pulley 901 can be understood by referring to FIGS. 9 and 10. The first and second pulley gears 503 and 402 may appear as shown in FIG. 9. FIG. 10 shows that the center drive pulley 901 contains ribbed slots 902 that correspond to protrusions 1000 (FIG. 9) of the first and second pulley gears 503, 402. The multiple side protrusions 1000 of the first and second pulley gears 503, 402 (FIG. 9) slide into the ribbed slots 902 located on the side of the center drive pulley 901 (FIG. 10) to lockably engage with each other. The engagement may be such that when the locked first pulley gear 503 or locked second pulley gear 402 rotates, the center drive pulley 901 will rotate in the same direction, thereby transferring the motion of the pulley gears 503, 402 to the drive pulley 901 and belt 1201.

The belt 1201 is shown in FIG. 4 to be wrapped around three pulleys 1211, 1212 and 901. Pulleys 1211 and 1212 may help transfer gear movement into belt movement. Center drive pulley 901 engages with one of the first gear set 500 and the second gear set 400 to cause rotational movement of the belt 1201. Although a three pulley system is shown, more than three pulleys or less than three pulleys are contemplated.

Idlers 1215 and 1216 (FIG. 4) may help to provide wrapping a sufficient amount of the belt 1201 around the center drive pulley 901 for the purpose of preventing belt 1201 slippage from the center drive pulley 901. Referring to FIG. 4, the belt 1201 wraps around idler 1215 and then proceeds down and around the center drive pulley 901. The belt 1201 then proceeds up and around the top of idler 1216. FIG. 4 shows that the idlers 1215, 1216 help the belt 1201 to wrap around more than 180° of the center drive pulley 901.

The gear mechanism for resheathing (i.e., the outer catheter 1200 moving from the proximal direction to the distal direction as indicated by the arrow in FIG. 4) will now be explained. Reference to the rotational movement of the various gears and pulleys will be made in accordance with perspective views facing the first gear set 500 (FIGS. 4, 8, 11, 12). The directional switch 101 is pushed such that the first pulley gear 503 is engaged with the center drive pulley 901 and the second pulley gear 402 is disengaged from the center drive pulley 901 (FIG. 8). Pulling the trigger 102 in the proximal direction, as indicated by the arrow in FIG. 8, causes the main drive gear 701 to engage with the rack 709 (FIG. 12) of the trigger 102 (FIG. 11) and rotate in a clockwise direction (the three arrows in FIG. 12 around first drive gear 502 represent clockwise rotation). Because the main drive gear 701 is directly connected to the drive shaft 702, the drive shaft 702 also rotates in a clockwise direction. As the drive shaft 702 rotates in a clockwise direction, the first drive gear 502 and the second drive gear 401 also rotate in the same direction. The first drive gear 502 is engaged to the first idle gear 501 and therefore clockwise rotation of the first drive gear 502 causes the first idle gear 501 to rotate counterclockwise (FIG. 8). The first idle gear 501 is engaged to a first pulley gear 503. Accordingly, counterclockwise rotation of the first idle gear 501 causes the first pulley gear 503 to rotate clockwise (FIG. 8). Because the directional switch 101 has been pushed to engage the first pulley 503 with the center drive pulley 901 (FIG. 8), the center drive pulley 901 also rotates in the clockwise direction. With the belt 1201 winding around a center drive pulley 901, two idlers 1215 and 1216 pull in the belt 1201 around the center drive pulley 901, as shown in FIG. 4. The idlers 1215 and 1216 optimize the connection between the belt 1201 and the center drive pulley 901 to minimize slippage of the belt 1201 around the center drive pulley 901. Clockwise rotation of the center drive pulley 901 also causes the belt 1201 to rotate clockwise (FIG. 4). The clockwise rotation of the belt 1201 causes the shuttle 1202 and outer catheter 1200 attached thereto to resheath or move proximally to distally (FIG. 4).

When the trigger 102 has been deactivated so that the trigger 102 moves distally and returns to its original position, the drive shaft 702 and main drive gear 701 rotate counterclockwise and return to their original position. The drive shaft 702 is permitted to rotate counterclockwise within the one-directional roller clutch bearings 403, 504. However, roller clutch bearings 403, 504 prevent the left and right drive gears 401, 502 from rotating counterclockwise upon the trigger 102 being deactivated. Thus, the first and second drive gears 502 and 401 will remain in the position from which they have rotated clockwise after activation of the trigger 102. The effect of having the first drive gear and the second drive gears 502 and 401 rotate clockwise but not counterclockwise is that the outer catheter 1200 may continue to be incrementally moved in a proximal (i.e., retractable direction) or distal direction (i.e., resheathing direction). Accordingly, this unidirectional movement of the first and second drive gears 502 and 401 is converted into movement of the belt 1201.

The gear mechanism for retracting the outer catheter 1200 (i.e., the outer catheter 1200 moving from the distal direction to the proximal direction) will now be explained. Reference to the rotational movement of the various gears and pulleys will be made in accordance with perspective views facing the second gear set 400 (FIG. 3). The directional switch 101 is pushed such that the second pulley gear 402 is engaged with the center drive pulley 901 and the first pulley gear 503 is disengaged from the center drive pulley 901. Referring to FIG. 3, pulling the trigger 102 in the proximal direction as indicated by the arrow causes the main drive gear 701 to engage with the rack 709 (FIG. 11) of the trigger 102 and rotate in a counterclockwise direction. Because the main drive gear 701 is directly connected to the drive shaft 702, the drive shaft 702 also rotates in a counterclockwise direction. As the drive shaft 702 rotates in a counterclockwise direction, the first drive gear 502 and the second drive gear 401 rotate in the same direction. Because the second drive gear 401 is engaged to the second pulley gear 402, counterclockwise rotation of the second drive gear 402 causes the second pulley gear 402 to rotate clockwise (FIG. 3). The engagement of the second pulley gear 402 with the center drive pulley 901 causes the center drive pulley 901 to also rotate in a clockwise direction (FIG. 3).

Figure 13:
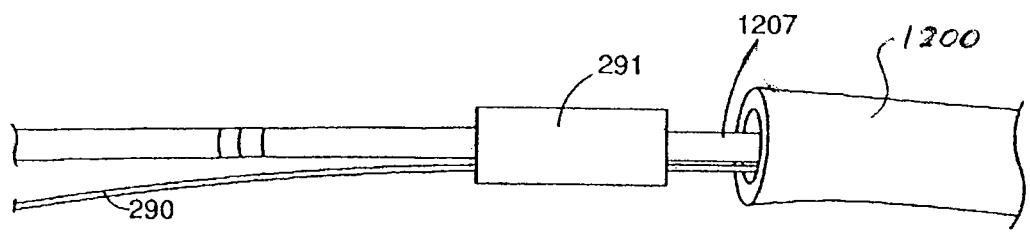
FIGS. 13-16 illustrate the steps of affixing one end of a retaining wire through the crowns of the stent.

Referring to FIG. 3, the rotation of the second pulley gear 402 with the center drive pulley 901, which was seen as clockwise from the perspective in FIG. 2, becomes viewed as counterclockwise from the perspective in FIG. 3. The counterclockwise rotation of the center drive pulley 901 also causes the belt 1201 to rotate counterclockwise. The counterclockwise rotation of the belt 1201 causes the shuttle 1202 and outer catheter 1200 attached thereto to retract or move distally to proximally (FIG. 12), thereby exposing the self-expanding prosthesis. As FIG. 13 shows, a step 1208 is formed where the smaller and larger diameter portions of the inner catheter 1207 meet, which prevents the prosthesis from being pulled back proximally with the outer sheath 1200.

The unidirectional movement of the first and second drive gears 502 and 401 is converted into proximal movement of the belt 1201 and outer catheter 1200 attached thereto. Specifically, when the trigger 102 has been deactivated so that the trigger 102 moves distally and returns to its original position, the drive shaft 702 and main drive gear 701 rotate clockwise with respect to FIG. 3 and return to their original position. The drive shaft 702 is permitted to rotate clockwise within the one-directional roller clutch bearings 403, 504. However, roller clutch bearings 403, 504 prevent the left and right drive gears 401, 502 from rotating upon the trigger 102 being deactivated. The effect of having the first drive gear and the second drive gears 502 and 401 rotate counterclockwise but not clockwise (as shown in FIG. 3) is that the outer catheter 1200 may continue to be incrementally moved in a proximal direction (i.e., retractable direction).

In order to prevent the self-expanding prostheses from moving as the outer catheter 1200 moves during resheathing, a stabilizing element is affixed to the prosthesis. The stabilizing element maintains the prosthesis in a substantially stationary position during the resheathing of the outer catheter 1200 over the prosthesis, as will now be explained.

Figure 14:
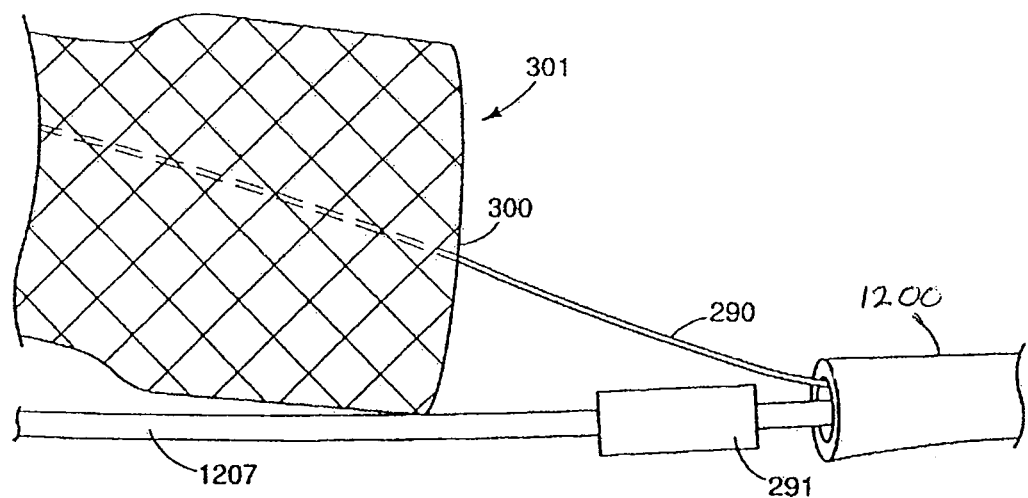
Figure 15:
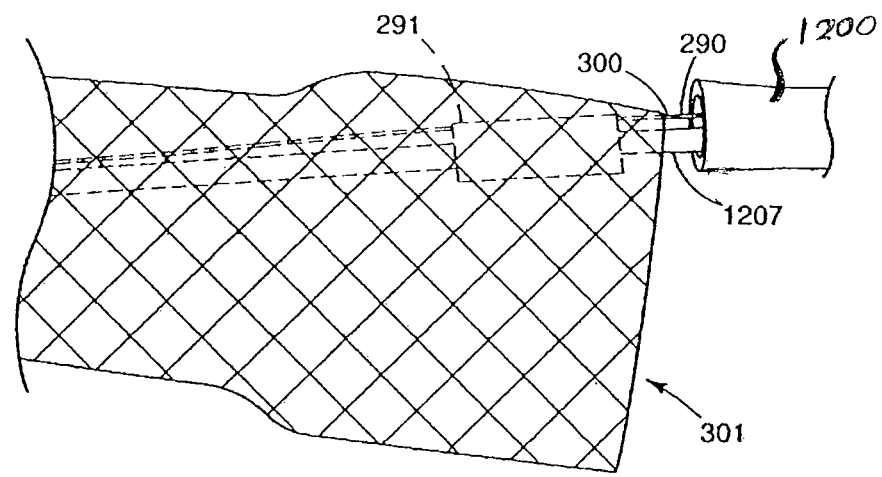
Figure 16:
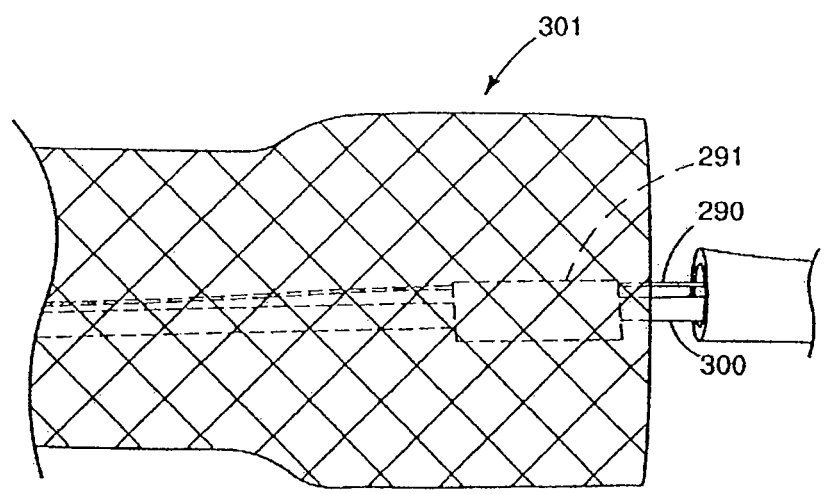
Figure 17:
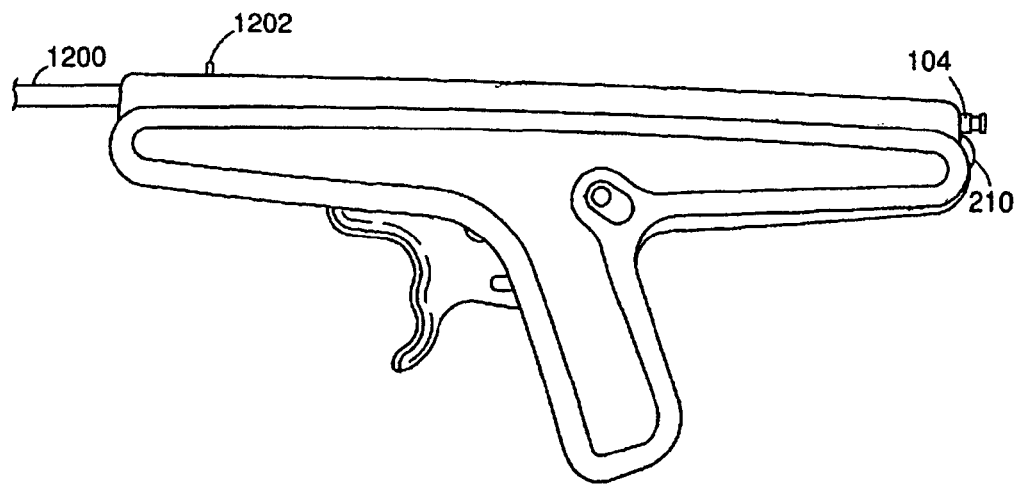
FIG. 17 is a perspective view of a handle portion of the delivery device.

Various types of stabilizing elements are contemplated. FIGS. 13-16 show the steps involved in loading and anchoring a preferred type of stabilizing element to a self-expanding stent. FIGS. 13-16 show that the stabilizing element may be a retaining wire 290. The proximal end of the retaining wire 290 is anchored to a ring 210 at the rear hub 104 of the inner catheter 1207, as shown in FIG. 17. The wire 290 extends along the longitudinal length of the device 100. The proximal portion of the wire 290 is disposed between the inner catheter 1207 and the outer catheter 1200. As the wire 290 extends distally from the rear hub 104, the wire 290 enters into a slit of the inner catheter 1207 and longitudinally travels therein in the distal direction until it emerges from the larger diameter portion of the inner catheter 1207 as shown in FIG. 14, which shows a stent 301 being loaded into the device 100. FIG. 14 shows that as the wire 290 emerges from the inner catheter 1207, it passes through one of the crowns 300 of a self-expanding stent 301. FIG. 14 shows that the wire 290 extends distally from the end portion of the stent 301 and may terminate at the body portion of the stent 301. At this juncture, the distal end of the wire 290 is maneuvered to extend through a lumen of a piece of bilumen tubing 291 (FIG. 15), which is affixed (e.g., glue) to the inner catheter 1207. The smaller diameter portion of the inner catheter 1207 is configured to extend through the proximal end of the stent 301 as shown in FIG. 15. The distal end of the wire 290 exits the lumen of the bilumen tubing 291. The distal end of the wire 290 is a free end that terminates within the lumen of the stent 301, as shown in FIGS. 15 and 16. The free end preferably does not interact with the stent 301.

The retaining wire 290 in this configuration (FIGS. 15 and 16) anchors the stent 301 in place such that the stent 301 will not move distally as the outer catheter 1200 is being resheathed over the stent 301. Specifically, referring to FIGS. 15 and 16, the stent 301 is locked into position at its proximal end by the crown 300 which the retaining wire 290 extends through. Referring to FIG. 16, the stent 301 cannot substantially move proximally because the stent 301 is locked by the wire 290 and the larger diameter portion of the inner catheter 1207. The stent 301 cannot substantially move distally because it is locked between the wire 290 and bilumen tubing 291. The stent 301 cannot substantially move up (i.e., coming out of the plane of the page) or down (i.e., going into the plane of the page) because the wire 290 passes through the crown 300. The stent 301 may not become free until the retaining wire 290 is removed from the crown 301. Removal of the retaining wire 290 may be achieved by pulling the ring 210 at the rear hub 104 of the inner catheter 1207, as shown in FIG. 17.

The bilumen tubing 291 may be positioned anywhere along the stent 301. In the example shown in FIGS. 13-16, the bilumen tubing 291 is positioned toward the proximal end of the stent 301 for the purpose of maximizing resheathing capabilities of the outer catheter 1200. In other words, the more the bilumen tubing 291 is positioned toward the distal end of the stent 301, the greater the tendency may be for the stent 301 to move with the outer catheter 1200 during resheathing. In the example shown in FIG. 15, the bilumen tubing 291 is affixed to the smaller inner catheter 1207 and positioned about 2 mm to about 5 mm from the proximal end of the stent 301. Accordingly, the amount of lateral movement of the stent 301 during resheathing of the outer catheter 1200 may be substantially eliminated.

Figure 18:
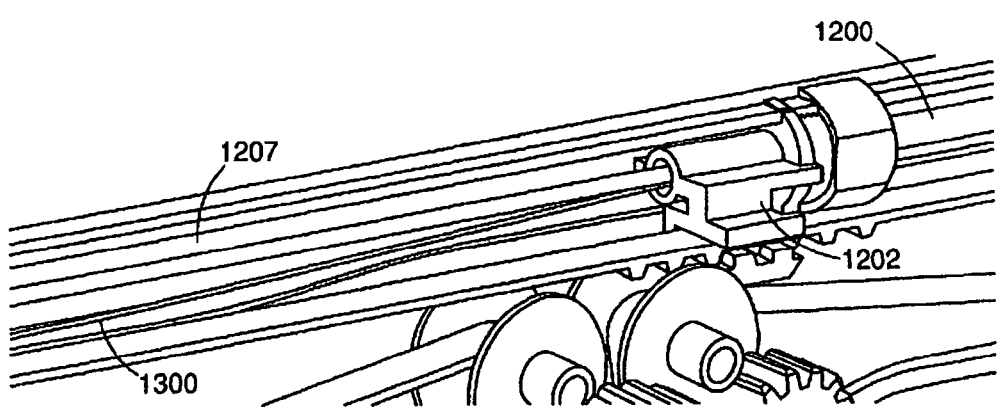
FIGS. 18-21 show an alternative stabilizing element for fixating the stent during the resheathing of the outer catheter.
Figure 19:
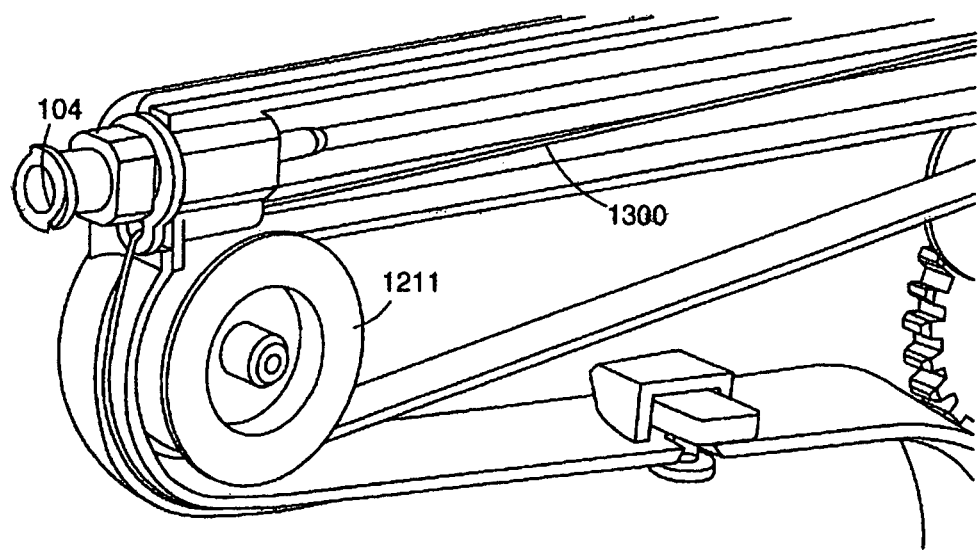
Figure 20:
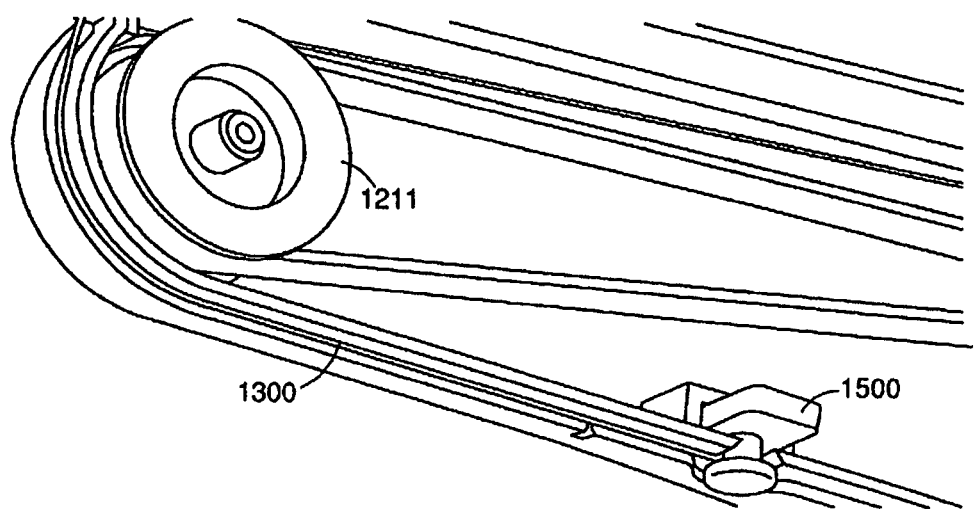
Figure 21:
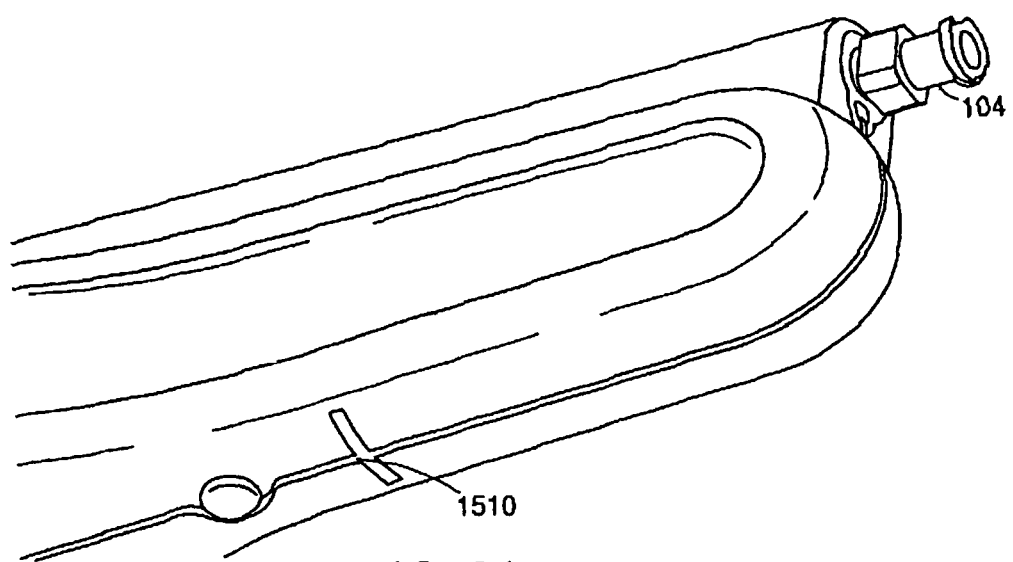

In an alternative embodiment, the stabilizing element is a suture loop 1300 may be used as shown in FIGS. 18-21. The suture loop 1300 may be looped through one or more crowns of the stent and is positioned in between the outer catheter 1200 and the inner catheter 1207. It may exit the shuttle 1202 as shown in FIG. 18. The suture loop 1300 continues to extend inside the device 100 between the inner catheter 1207 and the outer catheter 1200, as shown in FIG. 18. The suture loop 1300 exits the rear hub 104 as shown in FIG. 19. After exiting the rear hub 104, the suture loop 1300 follows a path where it is connected to the bottom of the device 100 at a post 1500 (FIG. 20). A groove 1510 (FIG. 21) located at the bottom of the device 100 may be used to cut the suture loop 1300. After the suture loop 1300 is cut, as shown in FIG. 21, the remainder of the suture loop 1300 can be pulled through the device 100 by pulling on one end of the suture 1300. Because the suture 1300 is held in place at the one or more crowns 300 of the stent and at the post 1500 of the handle (FIG. 20), the stent 301 may substantially be held in place during resheathing of the outer catheter 1200.

Figure 22:
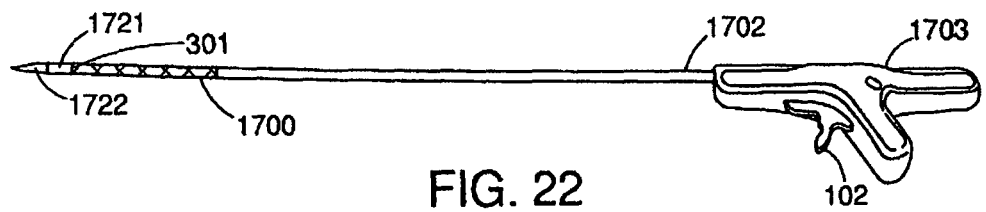
FIG. 22 shows the entire delivery device preloaded with an esophageal stent at the distal tip of the delivery section.

Having described the structure of the device 100 and the operation of the device 100 (i.e., the internal gear mechanism to retract/resheath the outer catheter 1200) and the various stabilization elements to fixate the stent 301 during the resheathing process, a method of use of the device 100 may now be described. The device 100 may be used to deploy various prostheses. As an example, a method of deploying an esophageal stent 301 will now be described. The esophageal stent 301 is loaded in between the inner catheter 1207 and the outer catheter 1200 along the distal end 1700 of the device 100, as shown in FIG. 22. Part of the loading process of the stent 301 involves affixing retaining wire 290 from one of the crowns 300 at the proximal end of the stent 301 to the rear hub 104 located at the proximal end of the device 100, as was described and shown in FIGS. 13-16.

Figure 23:
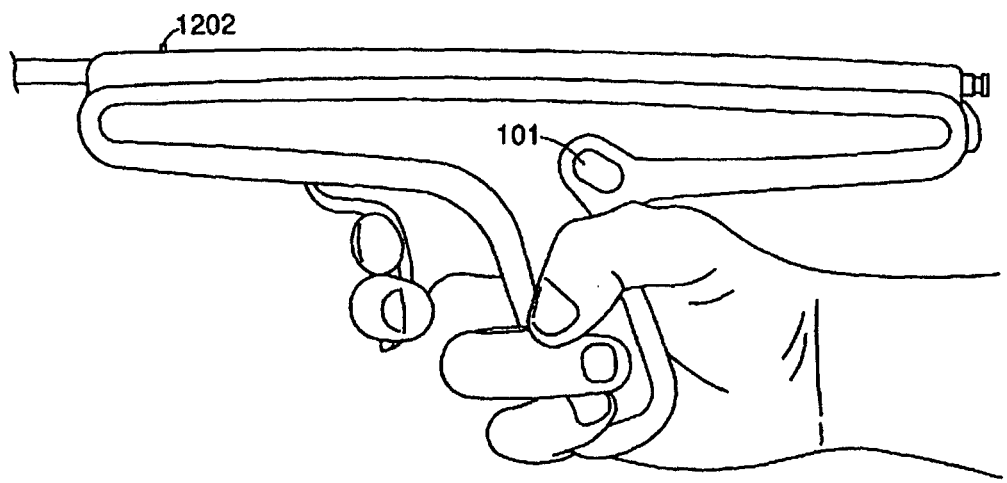
FIGS. 23-26 show a method of use of the delivery device.
Figure 24:
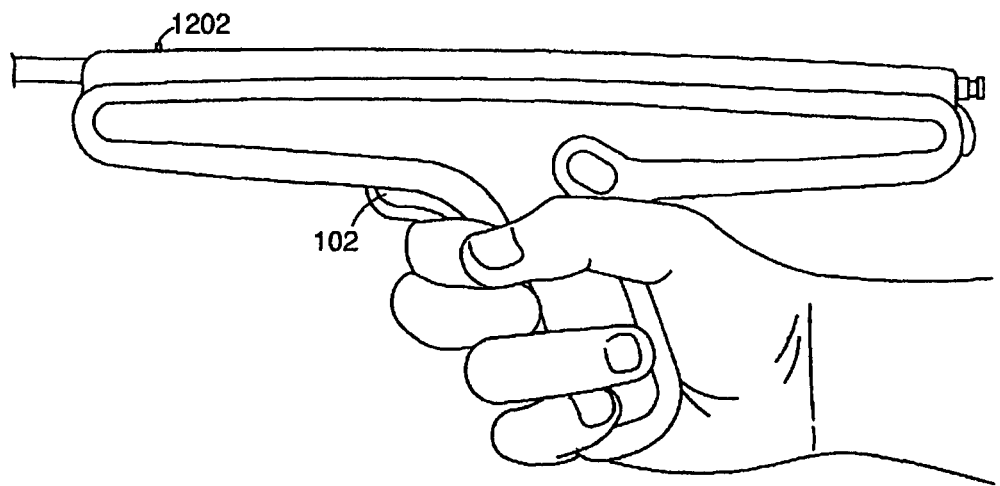
Figure 25:
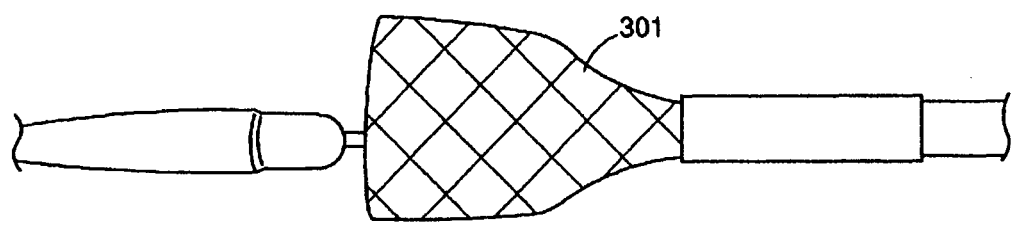
Figure 26:
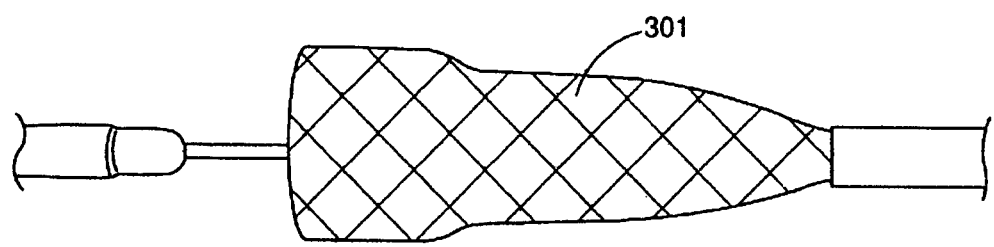

Having loaded the esophageal stent 301 and affixed the retaining wire 290 to the esophageal stent 301, the delivery and deployment process may begin. The delivery device 100 comprises a stent delivery section 1702 and an external manipulation section 1703. The delivery section 1702 travels through the body lumen during the procedure and delivers the prosthesis to a desired deployment site within the esophagus. The external manipulation section 1703 stays outside of the body during the procedure. The external manipulation section 1703 includes trigger 102 and can be manipulated by the physician with a single hand (FIG. 23) to position and release the stent 301 into the body lumen. After having delivered the delivery section 1702 of the delivery device 100 to the target site within the esophagus, the deployment of the stent 301 may begin. The trigger portion 102 of the device 100 will remain outside of the patient to enable deployment of the esophageal stent 301. The physician presses the directional switch 101 to actuate the second gear set 400 (FIG. 3) to enable proximal retraction of the outer catheter 1200 relative to the inner catheter 1207. FIG. 23 indicates that the shuttle 1202 is positioned near the distal end of the external manipulation section 1703. Having pressed the directional switch 101 to actuate the second gear set 400 with the center drive pulley 901, the physician may grasp the trigger 102 of the device 100 with a single hand, as shown in FIG. 23, to actuate the trigger 102 for the first time. The other hand may be free to perform other tasks. FIG. 24 indicates that the trigger 102 has been completely pulled backed in the proximal direction. In particular, the tip of the shuttle 1202 has proximally moved after one actuation of the trigger 102. With the second pulley gear 402 still mechanically coupled to the center drive pulley 901, trigger 102 is actuated multiple times to retract the outer catheter 1200 in the proximal direction relative to the inner catheter 1207 until a portion of the esophageal stent 301 has become exposed and partially radially expanded, as shown in FIG. 25. Further actuations of the trigger 102 cause the outer sheath 1200 to proximally move back even further, thereby exposing an increasing portion of the self-expanding stent 301, as shown in FIG. 26.

At this juncture, notwithstanding partial radial expansion of the stent 301, the device 100 may be activated to resheath the outer catheter 1200 over the stent 301 to allow repositioning of the stent 301 within the esophagus. The physician may need to resheath and reposition the stent 301 as a result of having placed the stent 301 in the incorrect position. The directional switch 101 may be pressed to disengage the center drive pulley from the second pulley gear and to engage the center drive pulley with the first pulley gear (FIG. 8). Having activated the first gear set 500 with the center drive pulley 901, actuation of the trigger 102 one or more times enables the outer sheath 1200 to move distally and resheath over the stent until the stent 301 is fully constrained back within the outer sheath 1200. With the stent 301 fully recaptured within the outer catheter 1200, the external manipulation section 1703 may be maneuvered to reposition the delivery section 1702 within the body lumen. After repositioning the delivery section 1702, the directional switch 101 may be reconfigured to reactivate the second gear set 400 with the center drive pulley 901 such that proximal retraction of the outer sheath 1200 occurs, thereby exposing the stent 301. The retaining wire 290 retains the stent 301 and prevents it from moving distally during resheathing.

Referring to FIG. 22, during deployment, the distal end 1700 of the outer catheter 1200 may comprise a transparent or translucent material (or a light-transmitting material) to enable the physician to visually observe the stent 301 and how it is positioned in relation to the esophageal stricture. FIG. 17 shows that the top-most portion of the shuttle 1202 protrudes through the housing of the device 100. The top-most portion of the shuttle 1202, as shown in FIG. 17, proximally moves back as the outer catheter 1200 is proximally retracted and may be used as a visual indicator to determine when resheathing capabilities have been lost. The distance that the top-most portion of the shuttle 1202 proximally moves back corresponds to the distance that the outer catheter 1200 has proximally retracted. The top-most portion of the shuttle 1202 can proximally move back a predetermined threshold distance beyond which the physician will realize that the outer catheter 1200 cannot be proximally retracted any further without losing the ability to resheath and recapture the stent 301 within the outer catheter 1200. Alternatively, the point at which the top-most portion of the shuttle 1202 aligns with a predetermined visual marker on the outer housing of the device 100 can also indicate the loss of the ability to sheath.

In an alternative embodiment, one or more radiopaque markers 1721 may be used under fluoroscopy to determine the distance the outer catheter 1200 has proximally retracted (FIG. 22). The radiopaque marker 1721 may be placed on the outer catheter 1200 between the distal tip 1722 and the distal end 1700 of the clear portion of the outer catheter 1200, as shown in FIG. 22. The one or more markers 1721 may be utilized to determine when the resheathing capabilities have been lost. For example, as the outer catheter 1200 is proximally retracted, the radiopaque marker 1721 may move along with it. The marker on the inner catheter 1207 (FIG. 1) may be positioned such that if the marker 1721 on the outer catheter 1200 aligns with the marker on the inner catheter 1207, the physician will realize that the stent 301 cannot be exposed any further without losing the ability to resheath and recapture the stent 301 within the outer catheter 1200.

As can be seen, the device 100 is capable of incrementally deploying the stent 301. In the above examples described, one full actuation of the trigger 102 may proximally move the belt 1201 and hence the outer sheath 1200 from about 5 mm to about 10 mm. Such incremental deployment may facilitate greater accuracy in positioning of the stent 301 at the target region. On the contrary, a conventional push-pull delivery device has less control as compared to the delivery device 100 because the conventional push-pull delivery device cannot withdraw the outer sheath in such small, precise increments. In fact, conventional push-pull delivery devices may typically pull back the outer sheath 1200 about 50 mm per actuation of the trigger, thereby increasing the likelihood of prematurely deploying the stent.

Another advantage of the device 100 as has been described is the ability to resheath the outer catheter 1200 over the stent 301. The resheathing feature gives the physician the ability to make real-time adjustments during the deployment procedure such that the stent may be repositioned. In the examples described, the stent 301 may be able to be resheathed even after about 10% of the stent 301 has been deployed or as much as about 95% of the stent 301 has been deployed. Yet other advantages include the ability to use a single hand to deploy the stent 301. The other hand may be free to perform other tasks, such as holding an endoscope when deploying a self-expandable stent therethrough.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. Furthermore, the advantages described above are not necessarily the only advantages of the invention, and it is not necessarily expected that all of the described advantages will be achieved with every embodiment of the invention.

The invention claimed is:

1. An apparatus for delivering an intraluminal device, comprising:
    a gear and pulley mechanism comprising a first gear set and a second gear set;
    a drive pulley adapted to be alternatively mechanically coupled to the first gear set and the second gear set; and
    a sheath disposed over an inner elongate member, the sheath being in mechanical communication with the drive pulley and adapted to retract in a proximal direction and resheath in a distal direction,
    wherein the drive pulley is configured to be mechanically coupled to the second gear set to move the sheath in a proximal direction relative to the inner elongate member to enable at least partial deployment of the intraluminal device,
    wherein the drive pulley is configured to be mechanically coupled to the first gear set to move the sheath in the distal direction relative to the inner elongate member to enable resheathing of a partially deployed intraluminal device, and
    further comprising a trigger, the trigger comprising a generally straight rack, the rack being translatable and adapted to engage with a main drive gear, the main drive gear being affixed to a drive shaft, wherein the first gear set comprises a first drive gear and the second gear set comprises a second drive gear, the first drive gear and the second drive gear each comprising one-directional roller clutch bearings, the drive shaft extending through the roller clutch bearings and mechanically coupled thereto, wherein the first drive gear engages a first idle gear, and the first idle gear engages a first pulley gear, wherein the second drive gear engages a second pulley gear, the first pulley gear and the second pulley gear being adapted to rotate in opposite directions in response to translation of the rack, the drive pulley being adapted to be alternatively mechanically coupled to the first pulley gear and the second pulley gear, and further wherein a pulley shaft extends through each of the first pulley gear, the second pulley gear, and the drive pulley, the first pulley gear and the second pulley gear each being translatable relative to the drive pulley along an axis of the pulley shaft, wherein a first directional switch is aligned with the axis of the pulley shaft and coupled to the first pulley gear, the first directional switch being adapted to simultaneously move the first pulley gear into engagement with the drive pulley and the second pulley gear out of engagement with the drive pulley, and wherein a second directional switch is aligned with the axis of the pulley shaft and coupled to the second pulley gear, the second directional switch being adapted to simultaneously move the second pulley gear into engagement with the drive pulley and the first pulley gear out of engagement with the drive pulley.

2. The apparatus of claim 1, wherein the sheath is capable of resheathing the intraluminal device after being up to about 95% deployed.

3. The apparatus of claim 1, further comprising a stabilizing element extending along a longitudinal axis of the inner elongate member and the sheath, the stabilizing element fixating the position of the intraluminal device during movement of the sheath relative to the inner elongate member.

4. The apparatus of claim 3, wherein the stabilizing element is a retaining wire configured to be mechanically engaged with the intraluminal device, the retaining wire being proximally movable to disengage from the intraluminal device.

5. The apparatus of claim 1, wherein a belt is wound around the drive pulley and coupled to the sheath.

6. The apparatus of claim 5, further comprising a shuttle fixedly connected to a straight length of the belt and fixedly connected to the sheath, the belt thereby translating longitudinal movement to the sheath along the straight length of the belt as the belt is driven by the drive pulley.

7. The apparatus of claim 6, wherein the belt comprises a first set of teeth adapted to engage with a second set of teeth of the shuttle.

8. The apparatus of claim 6, wherein the shuttle comprises an opening receiving the inner elongate member therethrough, the inner elongate member extending towards a proximal end of the apparatus, the inner elongate member being fixedly connected to the proximal end of the apparatus.

9. The apparatus of claim 8, wherein a proximal end of the inner elongate member comprises a luer fitting, a lumen extending through each of the luer fitting and the inner elongate member.

10. The apparatus of claim 1, wherein the first pulley gear and the second pulley gear are each slidable along the pulley shaft to engage and disengage with the drive pulley.

11. The apparatus of claim 1, the sheath being coupled to a belt, the belt being wound around at least 180 degrees of the drive pulley to prevent substantial slippage there between.

12. The apparatus of claim 11, wherein the belt comprises teeth that engage teeth of the drive pulley.

13. The apparatus of claim 11, further comprising two idlers, the two idlers being disposed on opposite sides of the drive pulley and configured to wrap the belt around the drive pulley.

14. An apparatus for delivering an intraluminal device, comprising:
    a gear and pulley mechanism comprising a first gear set and a second gear set, the first gear set and the second gear set each comprising a plurality of gears rotatable about parallel axes;
    an inner elongate member, the inner elongate member being fixed at a proximal end to a handle assembly;
    an outer elongate sheath disposed over the inner elongate member, the outer elongate sheath being coupled to a belt wound around a drive pulley, the outer elongate sheath adapted to be actuated by the first gear set rotating the drive pulley in a first rotational direction so as to move the elongate outer sheath in a distal direction relative to the inner elongate member, the outer elongate sheath being adapted to be actuated by the second gear set rotating the drive pulley in a second rotational direction opposite the first rotational direction so as to move the elongate outer sheath in a proximal direction relative to the inner elongate member; and
    a stabilizing element extending along a longitudinal axis of the inner elongate member and the outer elongate sheath for fixating the position of the intraluminal device during movement of the outer elongate sheath relative to the inner elongate member, wherein the stabilizing element is an elongate retaining wire configured to be mechanically engaged with the intraluminal device, the retaining wire passing through a proximal crown of the intraluminal device, the retaining wire being proximally movable to disengage from the proximal crown of the intraluminal device;
    wherein the first gear set comprises an idle gear, the idle gear mechanically coupled to a first pulley gear;
    wherein the second gear set comprises a second drive gear mechanically coupled to a second pulley gear; and
    wherein the drive pulley is adapted to be alternatively mechanically coupled to the first pulley gear and the second pulley gear, wherein a pulley shaft extends through each of the first pulley gear, the second pulley gear, and the drive pulley, the first pulley gear and the second pulley gear each being translatable relative to the drive pulley along an axis of the pulley shaft, wherein a first directional switch is aligned with the axis of the pulley shaft and coupled to the first pulley gear, the first directional switch being adapted to simultaneously move the first pulley gear into engagement with the drive pulley and the second pulley clear out of engagement with the drive pulley, and wherein a second directional switch is aligned with the axis of the pulley shaft and coupled to the second pulley gear, the second directional switch being adapted to simultaneously move the second pulley gear into engagement with the drive pulley and the first pulley gear out of engagement with the drive pulley.

15. The apparatus of claim 14, wherein the first pulley gear is adapted to be removably mechanically coupled to the drive pulley to drive the outer elongate sheath in a distal direction relative to the inner elongate member.

16. The apparatus of claim 14, wherein the second pulley gear is adapted to be removably mechanically coupled to the drive pulley to drive the outer elongate sheath in a proximal direction relative to the inner elongate member.

17. The apparatus of claim 14, further comprising a trigger comprising a rack engaging a main drive gear, the main drive gear being mechanically coupled to a first drive gear and a second drive gear, wherein the first drive gear is mechanically coupled to the idle gear and the second drive gear is mechanically coupled to the second pulley gear.

18. The apparatus of claim 17, wherein the first drive gear and the second drive gear each comprise one-directional roller clutch bearings.

19. The apparatus of claim 14, wherein the drive pulley is adapted to be removably mechanically coupled to one of the first gear set and the second gear set.

20. The apparatus of claim 14, further comprising the intraluminal device, wherein the intraluminal device is a self-expanding stent, the self-expanding stent being disposed between the inner elongate member and the outer elongate sheath.

21. A method for resheathing an intraluminal device, comprising the steps of:
  (a) providing an intraluminal device and a delivery apparatus comprising:
    a gear and pulley mechanism comprising a first gear set and a second gear set;
    a drive pulley adapted to be alternatively mechanically coupled to the first gear set and the second gear set;
    a retractable sheath disposed over an inner elongate member, the retractable sheath mechanically coupled to the drive pulley by a belt; and
    wherein the drive pulley is adapted to be alternatively mechanically coupled to a first pulley gear of the first gear set and the second pulley gear of the second gear set, wherein a pulley shaft extends through each of the first pulley gear, the second pulley gear, and the drive pulley, the first pulley gear and the second pulley gear each being translatable relative to the drive pulley along an axis of the pulley shaft, wherein a first directional switch is aligned with the axis of the pulley shaft and coupled to the first pulley gear, the first directional switch being adapted to simultaneously move the first pulley gear into engagement with the drive pulley and the second pulley clear out of engagement with the drive pulley, and wherein a second directional switch is aligned with the axis of the pulley shaft and coupled to the second pulley gear, the second directional switch being adapted to simultaneously move the second pulley gear into engagement with the drive pulley and the first pulley gear out of engagement with the drive pulley;
  (b) translating the second pulley gear of the second gear set into engagement with the drive pulley;
  (c) activating a trigger to cause the drive pulley to rotate the belt with the sheath thereon in a proximal direction relative to the inner elongate member so as to partially deploy the intraluminal device;
  (d) translating the first pulley gear of the first gear set into engagement with the drive pulley with the first gear set; and
  (e) activating the trigger to cause the drive pulley to rotate the belt with the sheath thereon in a distal direction relative to the inner elongate member so as to resheath the partially deployed intraluminal device.

22. The method of claim 21, wherein steps (c) and (e) each further comprise the step of
  fixating the position of the intraluminal device during movement of the retractable sheath relative to the inner elongate member with a stabilizing element.

23. The method of claim 22, further comprising the steps of:
  (f) re-translating the second pulley into re-engagement with the drive pulley and activating the trigger to proximally retract the outer sheath until the intraluminal device is fully exposed; and
  (g) withdrawing the stabilizing element to fully release the intraluminal device from the delivery apparatus into a body lumen.

24. The method of claim 21, wherein step (c) further comprises the step of
  determining a point at which the outer sheath cannot be resheathed by monitoring a top-most portion of a shuttle.

* * * * *

UNITED STATES PATENT AND TRADEMARK OFFICE
CERTIFICATE OF CORRECTION

PATENT NO.        : 9,149,379 B2                                    Page 1 of 1
APPLICATION NO.   : 11/879176
DATED             : October 6, 2015
INVENTOR(S)       : Fionan Keady et al.

It is certified that error appears in the above-identified patent and that said Letters Patent is hereby corrected as shown below:

<u>In the Claims</u>

In column 12, claim 14, line 53, replace "clear" with --gear--.

In column 14, claim 21, line 2, replace "clear" with --gear--.

Signed and Sealed this
Twenty-eighth Day of June, 2016

Michelle K. Lee
*Director of the United States Patent and Trademark Office*